United States Patent [19]

Sausse

[11] 4,024,059
[45] May 17, 1977

[54] ARTIFICIAL KIDNEY

[75] Inventor: Andre Sausse, Sceaux, France

[73] Assignee: Rhone-Poulenc Industries, Paris, France

[22] Filed: Apr. 22, 1975

[21] Appl. No.: 570,356

[30] Foreign Application Priority Data

Apr. 23, 1974 France .................. 74.14007

[52] U.S. Cl. .............. 210/195 R; 210/257 M; 210/259; 210/321 B
[51] Int. Cl.² ....................... B01D 31/00
[58] Field of Search ............ 210/321, 23, 22, 195, 210/29, 37, 38, 494, 195 R, 259, 321, 257 M; 128/2.4 R, 2.4 E; 23/258.5 M

[56] References Cited

UNITED STATES PATENTS

| | | | |
|---|---|---|---|
| 3,669,880 | 6/1972 | Marantz et al. | 210/321 XK |
| 3,712,475 | 1/1973 | Martiney | 210/321 K |
| 3,727,612 | 4/1973 | Sayers et al. | 210/321 XK |
| 3,731,680 | 5/1973 | Wright et al. | 210/321 XK |
| 3,795,318 | 3/1974 | Crane et al. | 210/321 XK |
| 3,839,200 | 10/1974 | Gigou et al. | 210/321 K |

Primary Examiner—Frank A. Spear, Jr.
Assistant Examiner—Ferris H. Lander
Attorney, Agent, or Firm—Stevens, Davis, Miller & Mosher

[57] ABSTRACT

An artificial kidney in which blood is pumped to and from a first compartment of a dialysis apparatus and dialysis liquid is pumped to and from a second compartment thereof. The hydrodynamic resistance within these compartments is arranged so that one simultaneously maintains a first zone of the apparatus in which the pressure of the blood in the first compartment is higher than the pressure of dialysis liquid in the second compartment and a second zone in which the pressure of the blood in the first compartment is lower than the pressure of the dialysis liquid in the second compartment. By this means in the first zone ultrafiltration occurs from the blood to the dialysis liquid and in the second zone ultrafiltration occurs to inject materials back into the bloodstream from the dialysis liquid.

11 Claims, 4 Drawing Figures

ARTIFICIAL KIDNEY

The present invention relates to an artificial kidney including an apparatus having a selectively permeable membrane which makes it possible to effect dialysis and ultrafiltration operations simultaneously.

U.S. Pat. No. 3,619,423 describes an artificial kidney consisting of the combination of a haemodialyser and an ultrafilter, in which the dialysis liquid is regenerated by enzymes and recycled.

However, the products resulting from decomposition due to the enzymes can be toxic and of sufficiently low molecular weights to enable them to be returned to the blood (for example ammonia). Some enzymes are dangerous and, should the membrane of the ultrafilter be accidentally perforated, they can pass into the venous blood. Furthermore, it is difficult to withdraw water from the patient without at the same time withdrawing the useful constituents of the ultrafiltrate.

It has also been proposed to employ a diafiltration procedure (compare TRANS. AMER. Soc. Artif. Int. Organs, 1970, pages 107–112), this being a technique which consists of introducing a dilution liquid of suitable composition into the blood and then of ultrafiltering the mixture obtained, whilst controlling the weight of the patient. However, it is obvious that great precautions must be taken regarding the sterility and the composition of the dilution liquid.

According to the present invention there is provided an artificial kidney comprising a dialysis apparatus, at least one dialysis membrane separating said apparatus into a first compartment and a second compartment, a blood inlet and a blood outlet for the first compartment, a dialysis liquid inlet and a dialysis outlet for the second compartment, a constant volume closed circuit system including said second compartment, a reservoir and a circulating pump connected to said dialysis liquid inlet and said dialysis liquid outlet, for circulating dialysis liquid therethrough, and means for preventing toxic waste materials being returned to said dialysis liquid inlet, a blood pump for pumping blood through said first chamber, and means for simultaneously maintaining a first zone of said dialysis apparatus, whereby the pressure of blood in said first compartment is higher than the pressure of dialysis liquid in said second compartment and a second zone in which the pressure of blood in said first compartment is lower than the pressure of dialysis liquid in said second compartment.

Such a kidney can be a simple and very efficient apparatus which provides great flexibility and especially great safety in use.

In order that the present invention will be better understood, the following description is given, merely by way of example, reference being made to the accompanying drawings, in which:-

Figure 3:
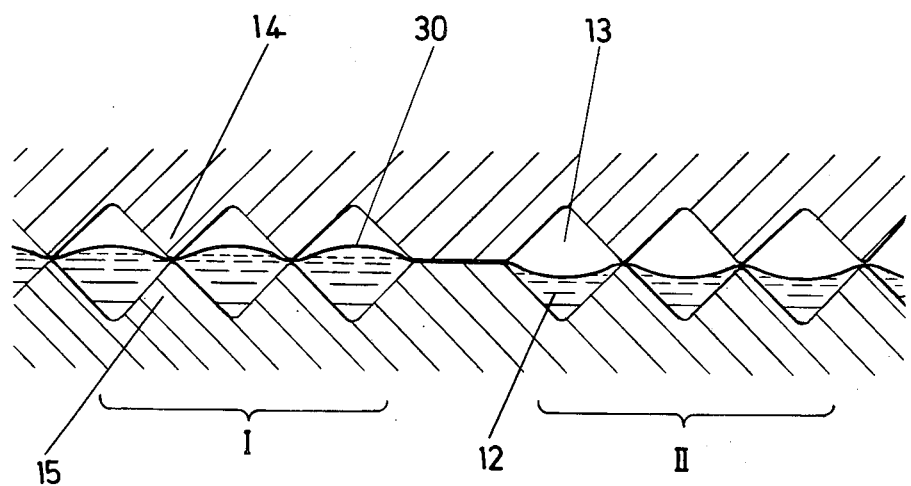
Figure 4:
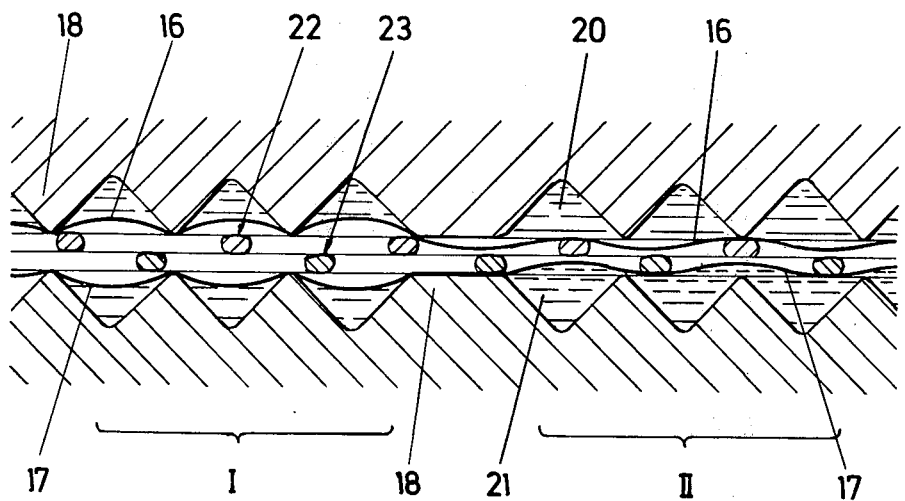

FIG. 3 is a partial view in cross-section of an apparatus having a single membrane, showing a method of supporting the membrane in the two ultrafiltration zones of the apparatus according to the invention; and FIG. 4 is a partial view in cross-section of an apparatus having two membranes, showing another method of supporting the membrane in the two ultrafiltration zones of the apparatus according to the invention.

Figure 1:
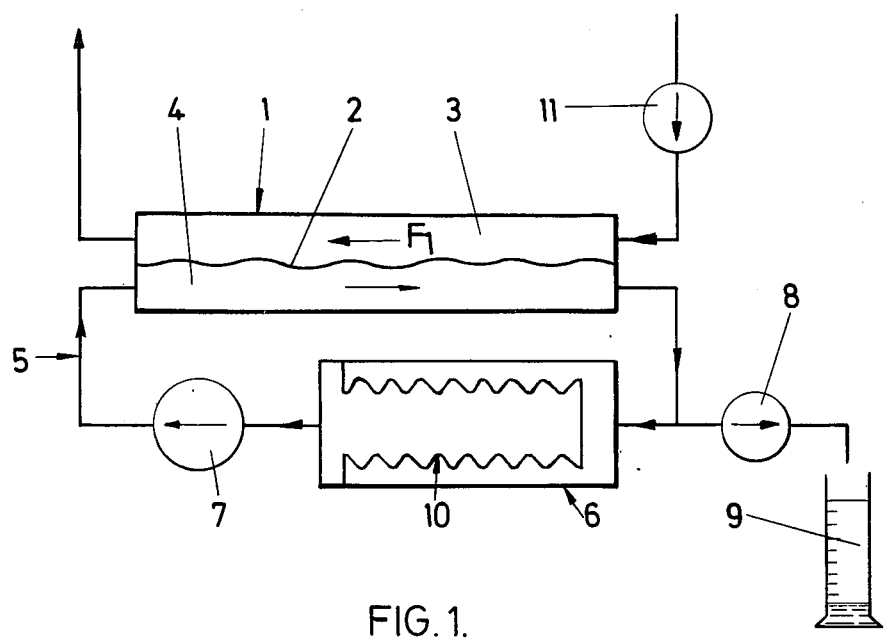
FIG. 1 is a diagram of one embodiment of dialysis liquid circuit according to the invention associated with an exchange apparatus having a membrane.

The artificial kidney represented in FIG. 1 comprises an apparatus 1 which generally consists of a haemodialyser having a membrane 2 which separates a compartment 3, through which a patient's blood is passed in the direction of the arrow $F_1$ by means of a pump 11, from a compartment 4 through which dialysis liquid is passed in counter-current. The dialysis liquid travels through a closed circuit 5 of constant volume, comprising a reservoir 6 and a circulating pump 7 of known type. The pump 8, connected to the outlet orifice of the apparatus 1, makes it possible to remove predetermined amounts of dialysis liquid from this circuit and to introduce them into a graduated container 9 which allows the amounts of liquid effectively removed to be controlled precisely.

In this circuit, the reservoir 6 is divided in a leakproof manner into two compartments by a flexible diaphragm 10 which can be deformed, for example under the effect of a slight pressure difference. Thus, fresh dialysis liquid situated to the left of the diaphragm 10 passes through the compartment 4 where it becomes charged with impurities which originated from the blood and which have passed through the membrane 2, and then it returns to the reservoir 6 to the right of the diaphragm 10, without becoming mixed with the fresh liquid.

Thus a limited volume of fresh dialysis liquid, free from waste materials, enters the apparatus 1. Since this apparatus is equipped with a selectively permeable membrane 2 which permits exchange of material simultaneously by haemodialysis and by ultrafiltration, it plays the roles of a haemodialyser and of an ultrafilter simultaneously.

Figure 2:
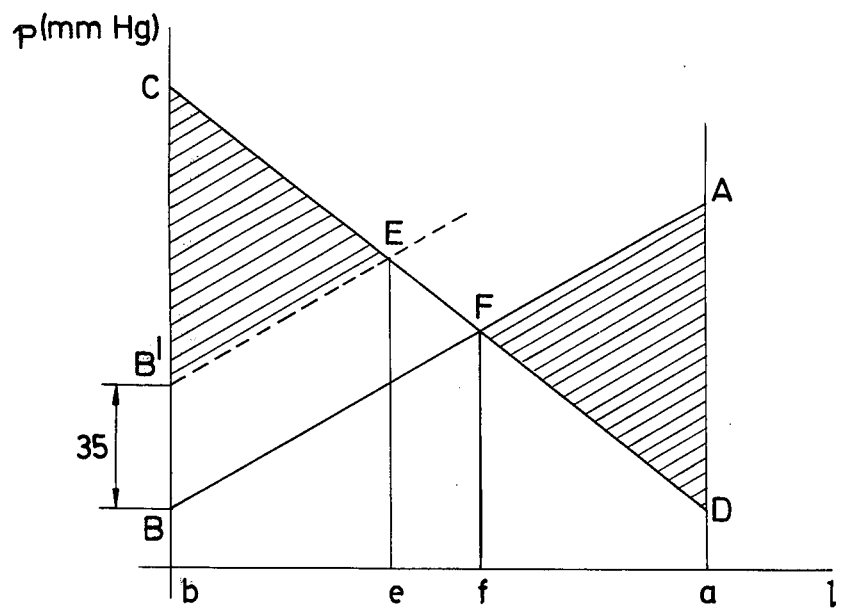
FIG. 2 is a graph of the pressure of the blood and the pressure of the dialysis liquid through the apparatus according to the invention, in the case of countercurrent circulation.

The graphs of the pressure of the blood and the pressure of the dialysis liquid, which are set up from one end of the apparatus to the other, in passing through an apparatus such as 1, have been plotted in FIG. 2. For simplification purposes, it is assumed that the pressure drops are constant over the entire length of the apparatus.

The blood enters at one end with an inlet pressure Aa and leaves at the opposite end with a reduced residual pressure Bb. Inside the apparatus, the pressure of the blood thus varies in accordance with the straight line segment AB. Likewise, the pressure of the dialysis liquid, which flows in counter-current to the blood, varies in accordance with the segment CD. It is seen in this graph that the two segments cut one another at F, inside the apparatus.

This means that, in contrast to the artificial kidneys of the prior art which comprise haemodialysers in which, for safety reasons, the dialysis liquid is always at a lower pressrue than the pressure of the blood, this apparatus permits the blood to be at a pressure higher than that of the dialysis liquid, at one end, and, at the opposite end, permits the dialysis liquid to be at a pressure higher than that of the blood.

In other words the apparatus 1 has two distinct zones, namely a zone (af)(f being the projection of F on the abscissa axis) where the pressure of the blood is higher than that of the dialysis liquid, and a zone (fb) where, conversely, it is the pressure of the dialysis liquid which is higher than that of the blood.

It might be thought that there is a danger involved in keeping the dialysis liquid at a pressure higher than that of the blood in a zone where it is separated from the blood only by a membrane. In fact, since the dialysis liquid occupies the closed circuit of constant volume, the accidental perforation of a membrane, which can be detected immediately by the sudden variations in pressure indicated by manometers (not shown) connected to the blood circuit and to the dialysis liquid circuit, does not lead to the dialysis liquid entering the blood to any substantial extent, nor to any great loss of blood. The artificial kidney according to the invention, thus operates very safely.

The apparatus 1 behaves like a haemodialyser throughout the zones (af and fb). Moreover, it behaves like a first ultrafilter in the zone (af), substances having a molecular weight lower than the cut-off zone of the membrane 2, corresponding, for example, to water, salts, urea, sugars and the like, travelling from the blood into the dialysis liquid under the effect of the pressure difference existing in this zone.

It might be expected that ultrafiltration in the opposite direction would occur throughout the entire zone (fb). In fact, blood contains various substances such as proteins, which are not present in the dialysis liquid and which, because their molecular weight is too high, cannot pass through the membrane. These substances create an osmotic pressure in the blood which has to be overcome in order to make ultrafiltration from the dialysis liquid to the blood possible. This osmotic pressure is the oncotic pressure; it is a constant substantially equal to 35 mm of mercury.

It follows that, if a line parallel to line AB is drawn, in the graph of FIG. 2, through B', the ordinate of which is 35 mm of mercury higher than that of B, this parallel line cutting CD at E, that is point having an abscissa e, only the zone (eb) corresponds to a second ultrafiltration zone, also called an injection zone, injection taking place from the dialysis liquid to the blood.

In the intermediate zone (fe) there is no ultrafiltration but only haemodialysis. In the zones (af) and (eb) there is, in addition to haemodialysis, ultrafiltration in a particular direction and in the opposite direction. The extent of ultrafiltration is proportional, witin each zone, to the cross hatched surface areas in FIG. 2. The zone (af) is situated in the vicinity of the two orifices corresponding to the introduction of the blood and to the removal of the dialysis liquid, and the zone (eb) is situated in the vicinity of the two orifices corresponding to the introduction of the dialysis liquid and to the removal of the blood.

The artificial kidney, which is represented diagrammatically in FIG. 1, operates in the following way. The blood to be purified passes through the haemodialyser 1 in the direction of the arrow $F_1$, preferably under the action of a peristaltic pump 11. The dialysis liquid, driven by the pump 7, passes through the haemodialyser in countercurrent to the blood. Purification of the blood is effected by haemodialysis and, moreover, by ultrafiltraion across the membrane 2.

In fact, in the zone of the apparatus 1 near the blood inlet, the blood transfers a part of the substances, which may be useful or toxic, and the molecular weight of which is less than the cut-off zone of the membrane 2, to the dialysis liquid, by ultrafiltration. The blood is thus subjected to a concentrating effect which can be pursued to the degree which is judged acceptable to enable the blood to be circulated inside the apparatus 1.

The ultrafiltrate is driven out of the haemodialyser into the reservoir 6. Its volume has then been adjusted (since the volume of the dialysis liquid closed circuit is constant) by the passage of useful (non-toxic) substances of molecular weight less than the cut-off zone of the membrane 2 and which are present in the fresh dialysis liquid, these being substances which undergo ultrafiltration in the opposite direction, namely into the blood, near the end of the aparatus situated on the side of the blood outlet.

The overall balance of the ultrafiltration process thus corresponds, at a first approximation, to the exclusive removal of toxic substances of low or medium molecular weights (such as urea, uric acid and the like), initially present in the blood.

However, to be strictly accurate, the flow rate of dialysis liquid removed by the pump 8 to the container 9 most be deducted from the flow rate of the second ultrafiltrate (from the dialysis liquid to the blood). This container receives a volume of liquid substantially equal to the volume of water which it is desired to withdraw from the patient during the treatment . It is thus optional whether all the useful substances ultrafiltered from the blood are replaced.

The means for employing the artificial kidney according to the present invention are very simple. Firstly, it is advantageous to use a semi-permeable dialysis membrane which is suitable for ultrafiltration and which preferably possesses a high level of ultrafiltration and a cut-off zone for molecules of molecular weight preferably between 6,000 and 60,000 and advantageously between 10,000 and 40,000. For example, the membranes described in French Pat. No. 2,105,502 are very suitable.

Secondly, in order to increase the ultrafiltrate flow rates, it is advantageous to convey the blood and the dialysis liquid to the haemodialyser at relatively high pressures and then to remove them at low pressures. This can be achieved by means of the various types of pumps usually employed. A peristaltic pump with only a slight haemolysing effect 11 can drive the blood from the patient into the apparatus 1, and the pump 7 can drive the dialysis liquid.

It is advantageous to use apparatuses which set up a high hydrodynamic resistance, produced by any known means, either to the blood, or to the dialysis liquid, or to both these liquids. Thus the liquids can be provided, by the compartments 3 and 4, only with passages, the cross-sections of which are, over lengths exceeding 60 cm and preferably 80 cm, less than the cross-section and preferably less than half of the cross-section of the piplines which are connected to the apparatus and which correspond to these liquids. Packings of any known types can fill these passages in order to increase the resistance to forward movement of the liquids. If desired, the pressure drops can have different values over the length of the apparatus. Relatively long and narrow apparatuses are generally used.

Although the dialysis liquid generally flows through the apparatus 1 and issues therefrom at pressures higher than atmospheric pressure, it is possible, if necessary, to remove the dialysis liquid from the haemodialyser at sub-atmospheric pressure, for example by means of an additional pump (not shown).

The artificial kidney according to the invention can be used with apparatuses, the membranes of which can have any of the shapes usually employed. Thus these membranes can be, for example, flat, tubular, in the form of spirals or in the form of hollow fibres, Since these apparatuses each comprise at least two zones in which the pressures are reversed, the membrane is thus acted upon in these zones on one face and then on the opposite face by the liquid at the higher pressure.

In apparatuses having flat membranes or membranes arranged in spirals, these membranes are positioned between supports and each membrane has each face in direct contact with these supports.

FIG. 3 is a partial cross-section of an apparatus having a single membrane. The membrane 30 separates the blood which flows through the grooves 12 from the dialysis liquid which flows through the opposite grooves 13. The membrane is in direct contact with the supports 14 and 15 opposite one another, and this makes it suitable both for the zone I in which the pressure of the blood is higher than that of the dialysis liquid, and for the zone II in which the pressure of the blood if lower than of the dialysis liquid. The membrane is curved in opposite directions in the zones I and II.

FIG. 4 is a partial cross-section of an apparatus having two membranes. The membranes 16 and 17, between which the blood flows, are held by supports 18 and 19 having grooves 20 and 21 through which the dialysis liquid flows. A spacer, which generally consists of a grid made up two crossed rows of heat-welded parallel yarns 22 and 23, separates the two membranes. This grid enables the membranes to be suitable both for the zone I where the pressure of the blood is higher than that of the dialysis liquid and zone II where the pressure of the blood is less than that of the dialysis liquid.

It can be advantageous to divide the apparatus up into at least two sub-assemblies corresponding to the two ultrafiltration zones, and to connect the corresponding compartments of each sub-assembly in series. Each sub-assembly has a well-defined structure and well-defined functions. These functions are, for example in the case of three sub-assemblies, haemodialysis and ultrafiltration; haemodialysis; and haemodialysis and injection (ultrafiltration in the opposite direction to the above). The sub-assemblies can be joined by channels provided, where appropriate, with means for adjustng their passage cross-section (for example, a valve) so as to increase the overall pressure drops, should this be necessary.

It is preferred to carry out the present inventon using apparatuses including a plurality of hollow fibres as the membrane, the membrane being thus self-supporting. It is possible to use any known type of apparatus provided with hollow fibres and any known type of hollow fibre having a semi-permeable wall.

As the apparatus including hollow fibres, those apparatuses are preferred in which the hollow fibres are grouped together in parallel bundles, the ends of each bundle being located in the two zones where reversed pressures prevail. p In FIG. 1, a dialysis circuit has been represented which is devoid of means for recycling the dialysis liquid. Means equivalent to those represented can be used to move the dialysis liquid: for example, a piston can move the dialysis liquid from one end to the other of a reservoir 6 in the form of a cylinder.

If desired, it is possible to recycle the dialysis liquid, subject to the condition that the liquid is purified in such a way that it is completely pure when it returns to the apparatus 1. Known techniques for regenerating dialysis liquid can be used for this purpose. Active charcoal can especially be used for fixing the waste materials which originated from the blood. It is particularly advantageous to place at least a part of the active charcoal inside the apparatus 1 in the compartment 4 through which the dialysis liquid passes. The active charcoal thus forms a packing which increases the resistance to flow of the dialysis liquid.

The value in recycling the dialysis liquid after it has been purified is to make it possible rigorously to restore to the patient — at least on a qualitative basis — all the useful substances of low or medium molecular weight which were removed from him in the first ultrafiltration zone. Current techniques hitherto only permitted arbitrary compensation which was frequently inadequate or inappropriate.

The artificial kidney according to the invention can, by way of the variant, be employed to curculate the blood and the dialysis liquid in co-current through the haemodialyser.

If, at the inlet of the haemodialyser, the pressure of the dialysis liquid is higher than that of the blood increased by the oncotic pressure at the outlet of the haemodialyser, the pressure of the blood must be higher than that of the dialysis liquid. In this case, it is found that the dialysis liquid undergoes ultrafiltration into the blood, the latter is thus first diluted, and then the blood undergoes ultrafiltration in its trun into the dialysis liquid, thus getting rid of its waste materials.

If, on the other hand, at the inlet of the haemodialyser, the pressure of the dialysis liquid is less than that of the blood, at the outlet of the haemodialyser the pressure of the dialysis liquid must be greater than that of the blood increased by the oncotic pressure. In this case, it is found that the blood undergoes ultrafiltration into the dialysis liquid and thus begins by undergoing concentration (as according to the process represented in FIG. 2); thereafter, it is the dialysis liquid which undergoes ultrafiltraton into the blood.

When using the artificial kidney according to the invention, it is not necessary to introduce beforehand, into the blood, a specially prepared and sterilised dilution liquid. Since the pressure drops desired are obtained easily by causing the blood and the dialysis liquid to flow at relatively high speeds, these speeds promote mixing operations and oppose clogging of the membrane. However, if desired, the artificial kidney according to the invention can possess means for periodically reversing the direction of flow of the dialysis liquid and/or of the blood in order to prevent possible clogging of the membrane.

The efficiency of the artificial kidney according to the invention is due in part to the fact that two-way ultrafiltration takes place in addition to haemodialysis, and this especially allows excellent transfer of the medium-size molecules. The overall ultrafiltration thus in practice removes only toxic substances, and can be adjusted independently of local ultrafiltrations; the loss in weight of the patient can thus be determined easily a priori. The artificial kidney according to the invention is very particularly suitable for cases of detoxication. If desired, it is possible, moreover, to inject known amount of solutions into the dialysis liquid circuit, before the inlet of the haemodialyser, by means of a metering pump (not shown). Finally, it is to be noted that only a fresh dialysis liquid, or an optionally regenerated dialysis liquid, can undergo ultrafiltration towards the blood, and this contributes towards the good yield of the aparatus.

I claim:

1. An artificial kidney comprising, in combination:-
   a. a dialysis apparatus;
   b. at least one dialysis membrane separating said apparatus into a first compartment and a second compartment;
   c. a blood inlet and a blood outlet for the first compartment;
   d. a dialysis liquid inlet and a dialysis liquid/outlet from the second compartment;
   e. a constant volume closed circuit system including said second compartment, a reservoir and a circulating pump connected to said dialysis liquid inlet and said dialysis liquid outlet, for circulating dialysis liquid therethrough, and means for preventing toxic waste materials being returned to said dialysis liquid inlet;
   f. a blood pump for pumping blood through said first chamber; and
   g. means for simultaneously maintaining a first zone of said dialysis apparatus, whereby the pressure of blood in said first compartment is higher that the pressure of dialysis liquid in said second compartment and a second zone in which the pressure of blood in said first compartment is lower than the pressure of dialysis liquid in said second compartment.

2. An artificial kidney as claimed in claim 1, wherein said first zone and said second zone are situated in the vicinity of said blood inlet and said blood outlet and said dialysis liquid inlet and said dialysis liquid outlet.

3. An artificial kidney as claimed in claim 1, wherein said blood inlet is situated adjacent to said dialysis liquid outlet and said blood outlet is situated adjacent said dialysis liquid inlet, whereby the blood and dialysis liquid passes through said apparatus in counter current, and further comprising means for making the blood enter the apparatus at a higher pressure than the outlet pressure of the dialysis liquid and for making the dialysis liquid enter at a pressure higher than the outlet pressure of the blood increased by the oncotic pressure of the membrane.

4. An artificial kidney as claimed in claim 1, wherein said means for simultaneously maintaining comprise said circulating pump and said blood pump and means for offering a hydrodynamic resistance to the flow of blood and/or dialysis liquid within said chambers.

5. An artificial kidney as claimed in claim 1, and further comprising pipelines leading to and from said first and second compartments and wherein the cross sections of the passages for flow of blood in the said first compartment and the flow of dialysis liquid in the said second compartment are, over lengths at least equal to 60 cm, less than those of said pipelines 6. An artificial kidney as claimed in claim 1, wherein the said dialysis membranes comprise self-supporting membranes consisting of a plurality of hollow fibres.

7. An artificial kidney as clamed in claim 1, further comprising means supportng said at least one dialysis membrane simultaneously on both faces thereof.

8. An artificial kidney as claimed in claim 7, wherein the membrane and support are divided up into at least two sub-assemblies, corresponding to said first zone and said second zone, the corresponding compartments of each sub-assembly being connected to one another directly in series.

9. An artificial kidney as claimed in claim 7, wherein said at least one membrane and support are divided up into at least two sub-assemblies corresponding to said first and second zones, corresponding compartments of each sub-assembly/and further comprising a channel and means for adjusting a cross-section of said channel, said channel connecting said compartments in series.

10. An artificial kidney as claimed in claim 1, and further comprising a diaphragm in said reservoir dividing said reservoir in a fluidtight manner to prevent toxic waste material being returned to said dialysis liquid inlet.

11. An artificial kidney as claimd in claim 1, and further comprising an activated charcoal device for preventing toxic waste materials being returned to said dialysis liquid inlet.

* * * * *